(12) United States Patent
Yoon et al.

(10) Patent No.: US 7,419,492 B2
(45) Date of Patent: Sep. 2, 2008

(54) T-SHAPED GAUGE AND ACETABULAR CUP NAVIGATION SYSTEM AND ACETABULAR CUP ALIGNING METHOD USING THE SAME

(75) Inventors: Yong-San Yoon, Daejeon (KR); Chung-Hee Won, Seoul (KR); Byung-Hoon Ko, Daejeon (KR); Youngbae Park, Cheongju-si (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 770 days.

(21) Appl. No.: 10/736,481

(22) Filed: Dec. 15, 2003

(65) Prior Publication Data
US 2004/0210233 A1    Oct. 21, 2004

(30) Foreign Application Priority Data
Apr. 21, 2003    (KR) .................... 10-2003-0025136

(51) Int. Cl.
*A61B 17/58* (2006.01)
(52) U.S. Cl. .......................... 606/91; 606/102
(58) Field of Classification Search ................ 606/91, 606/96, 97, 102
See application file for complete search history.

(56) References Cited

U.S. PATENT DOCUMENTS

| | | | | | |
|---|---|---|---|---|---|
| 4,702,236 | A | * | 10/1987 | Tarabichy et al. | 606/86 |
| 5,141,512 | A | * | 8/1992 | Farmer et al. | 606/87 |
| 5,569,260 | A | * | 10/1996 | Petersen | 606/88 |
| 5,611,353 | A | * | 3/1997 | Dance et al. | 600/595 |
| 5,995,738 | A | * | 11/1999 | DiGioia, III et al. | 703/11 |

* cited by examiner

*Primary Examiner*—Eduardo C. Robert
*Assistant Examiner*—Jerry Cumberledge
(74) *Attorney, Agent, or Firm*—DeMont & Breyer LLC

(57) ABSTRACT

A T-shaped gauge and acetabular cup navigation system and acetabular cup aligning method using the T-shaped gauge, which can measure anatomical landmarks of the pelvis at the same time, calculate an anterior pelvic plane from the measured value, calculate a transformed anterior pelvic plane by converting the anterior pelvic plane in comparison with a pelvic reference frame, and set a direction vector of an acetabular cup on the transformed anterior pelvic plane, thereby exactly inserting the acetabular cup into the acetabulum without regard to movement of the pelvis.

2 Claims, 8 Drawing Sheets

T-SHAPED GAUGE AND ACETABULAR CUP NAVIGATION SYSTEM AND ACETABULAR CUP ALIGNING METHOD USING THE SAME

CROSS-REFERENCE TO RELATED APPLICATIONS

This application claims priority of Republic of Korea patent application number KR 10-2003-0025136, filed 21 Apr. 2003.

BACKGROUND OF THE INVENTION

1. Field of the Invention

The present invention relates to an acetabular cup navigation system for calculating an insertion direction of an acetabular cup inserted into the pelvis for total hip replacement surgery, and more particularly, to a T-shaped gauge and acetabular cup navigation system and acetabular cup aligning method using the T-shaped gauge for exactly calculating an insertion direction of an acetabular cup, which will be inserted into the pelvis, by measuring anatomical landmarks of the pelvis at once and measuring pelvis coordinates changed during surgery in real time.

2. Background of the Related Art

In a conventional artificial joint surgery for replacing hip joints with artificial joints, the artificial joints could not be inserted into the hip joints in an exact orientation (or angle) because the orientation (or angle) of the the artificial joints inserted into the hip joints is defined by a doctor's experiences and a mechanical gauge provided by an artificial joint manufacturer. Furthermore, as patients' pelvis sizes and shapes are different according to the patents' body conditions, the artificial joints cannot be inserted into the hip joints in the exact orientation (or angle). If the artificial joints are inserted into the hip joints in a deviated orientation from the normal orientation, the patent who undergoes artificial joint surgery has to experience surgery again so that the artificial joints are located at an exact orientation of the hip joints.

Therefore, to address the above problem, a navigation system for surgery of hip joints is induced so that the doctor can obtain information of alignment of artificial joints inserted into the hip joints in real time during the surgery. The navigation system is used to match the artificial joints to the patient's pelvis based on three-dimensional image of the patient's pelvis part obtained through a CT scan. For example, for total hip replacement surgery, the navigation system is used to determine a orientation of an acetabular cup inserted into the acetabulum of the pelvis based on an anterior pelvic plane formed by three points, which are called as anterior superior iliac spines and pubis part.

In order to operate the artificial joints using the conventional navigation system, there is a need for a registration of making a transformation matrix of the exact position of the pelvis for the surgery of the artificial joints using image information of the patient's pelvis obtained by the CT scan. To carry out the above process, a fiducial marker is inserted into the patient's pelvis before surgery to measure the corresponding position, or points of several tens are measured at the pelvis part of a cut part during the surgery. Moreover, the CT scan may have an adverse influence on the patient's health and is very expensive as using radial rays at a corresponding region of the patient's body to be operated surgically to obtain the three-dimensional image.

Meanwhile, to solve the disadvantages of the CT scan, directly before the surgery of the artificial joints, using a measuring device, the three anatomical landmarks of the pelvis are measured on the skin corresponding to the patient's pelvis position, and then, the surgery of the artificial joints is performed based on the three anatomical landmarks.

However, as the measuring device measures the three anatomical landmarks respectively, the measured anatomical landmarks have a relatively measuring deviation by the hypodermic fat. Therefore, the artificial joint surgery using the measuring device may considerably deteriorate accuracy to exactly insert the acetabular cup into the acetabulum, and the patient who has been operated has to be operated again to correct the orientation of the artificial joints.

SUMMARY OF THE INVENTION

Accordingly, the present invention has been made in view of the above problems, and it an object of the present invention is to provide a T-shaped gauge used for measuring anatomical landmarks of the pelvis at the same time and calculating a reference value of an insertion orientation of an acetabular cup inserted into the pelvis.

Another object of the present invention is to provide an acetabular cup navigation system and an acetabular cup aligning method using the T-shaped gauge, which can calculate the insertion orientation of the acetabular cup inserted into the pelvis in real time during surgery and exactly align the acetabular cup into the pelvis by making a transformed anterior pelvic plane fixed into the pelvis and setting a orientation vector of the acetabular cup on the transformed anterior pelvic plane using the anterior pelvic plane formed by the measured anatomical landmarks of the pelvis and a pelvic reference frame formed on the pelvis in itself.

To achieve these objects, according to the present invention, there is a T-shaped gauge including: first to third probe rods fixed at three positions of the pelvis; a T-shaped supporter slidably connected to the probe rods to change the first plane formed by the three positions, the T-shaped supporter being supported from the first plane to a predetermined height by the probe rods; a first dynamic reference base separably mounted at a portion of the T-shaped supporter, the first dynamic reference base emitting light to indicate the first plane; and a moving part moved symmetrically from the T-shaped supporter by the first and second probe rods.

In another aspect of the present invention, an acetabular cup navigation system using the T-shaped gauge includes: a T-shaped gauge for measuring anatomical landmarks of the pelvis at the same time; a first dynamic reference base fixed at the first position of the pelvis for indicating a position of the pelvis by emitting light; an acetabular cup positioner fixed at the second position of the pelvis for indicating a position of an acetabular cup; a photodetector for detecting light emitted from the T-shaped gauge, light emitted from the first dynamic reference base, and light emitted from the acetabular cup positioner; and a controller for producing an anterior pelvic plane from the first detection signal, which is outputted from the photodetector and made by the light emitted from the T-shaped gauge, producing a pelvic reference frame from the second detection signal by the light emitted from the first dynamic reference base, and producing a orientation vector of the acetabular cup positioner by the light emitted from the acetabular cup positioner.

In another aspect of the present invention, there is also provided an acetabular cup aligning method using a T-shaped gauge including the steps of: calculating an anterior pelvic plane from anatomical landmarks of the pelvis; calculating a pelvic reference frame by a position of the pelvis; converting the anterior pelvic plane based on the pelvic reference frame and producing a converted anterior pelvic plane; and setting a orientation vector of an acetabular cup, which was obtained previously, on the converted anterior pelvic plane.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will now be made in detail to the preferred embodiments of the present invention, examples of which are illustrated in the accompanying drawings.

Figure 1A:
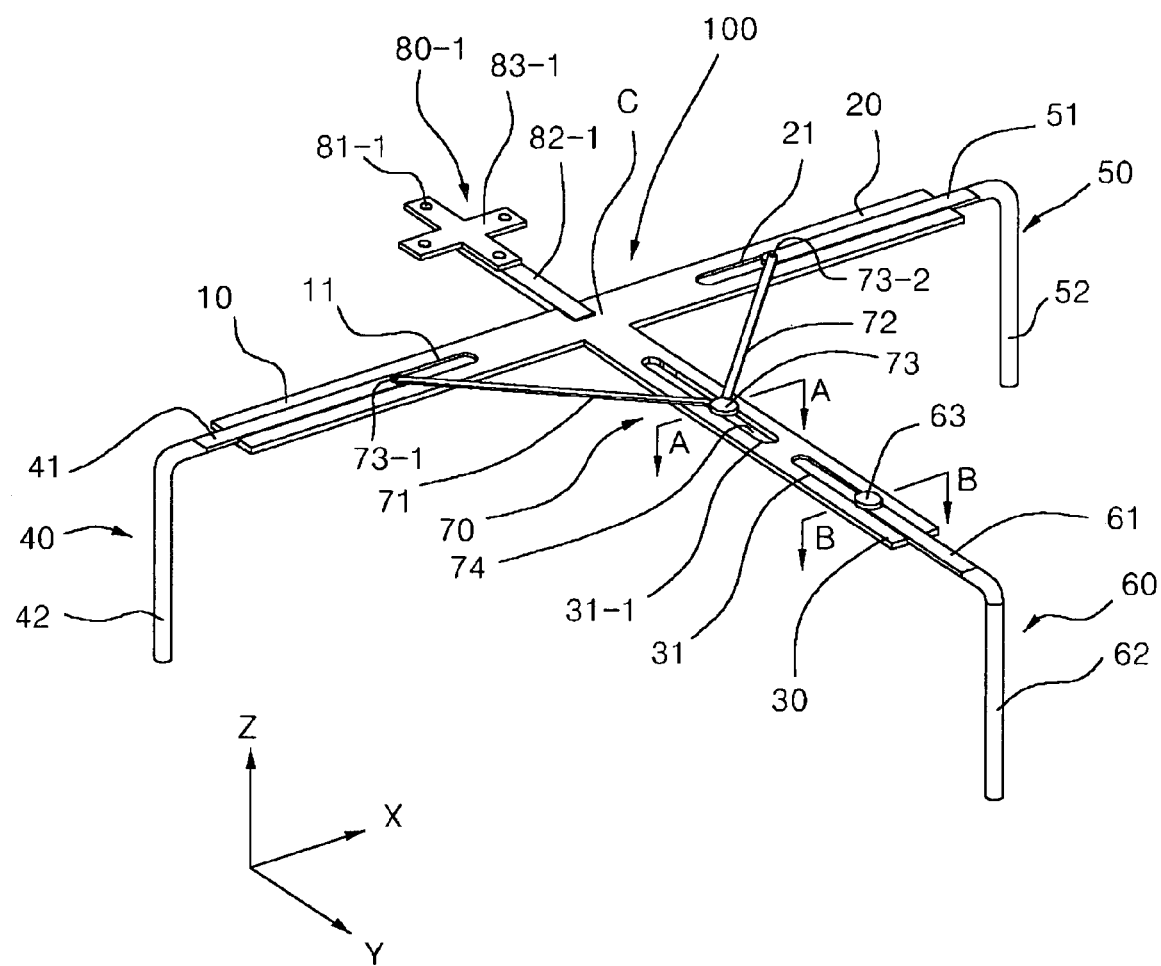
FIG. 1A is a perspective view of a T-shaped gauge according to the present invention.
Figure 1B:
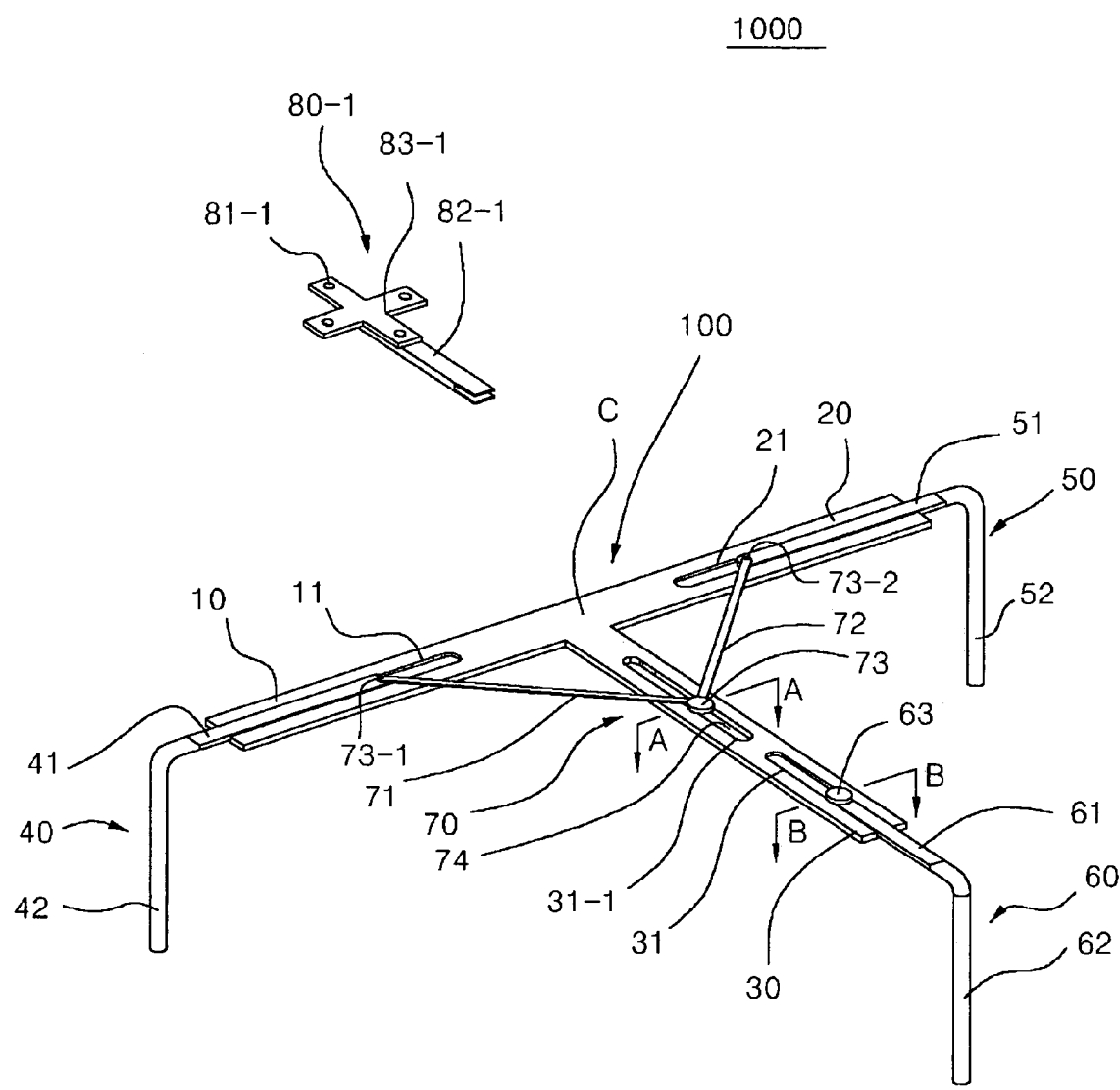
FIG. 1B is a perspective view of the T-shaped gauge in a state in which the first dynamic reference base is separated.

FIG. 1A is a perspective view of a T-shaped gauge according to the present invention, and FIG. 1B is a perspective view of the T-shaped gauge in a state in which the first dynamic reference base is separated. The T-shaped gauge includes: first to third probe rods 40, 50 and 60 located at anatomical landmarks of the pelvis at the same time, which are two anterior superior iliac spine (ASIS) and a pubis part; a T-shaped supporter 100 slidably connected to the first to third probe rods 40, 50 and 60 and supported from the anatomical landmarks to a predetermined height by the probe rods 40, 50 and 60; a first dynamic reference base 80-1 separably adhered on a portion of the T-shaped supporter 100 for indicating the horizontal level of the T-shaped supporter 100; and a moving part 70 for allowing the first and second probe rods 40 and 50 to move symmetrically from the T-shaped supporter 100.

The T-shaped supporter 100 includes: first and second guide bars 10 and 20 of predetermined widths, the guide bars 10 and 20 being formed at the coaxial line on the same plane and extending from a center point C toward both sides thereof to predetermined lengths; and a third guide bar 30 of a predetermined width located on the same plane as the first and second guide bars 10 and 20 at right angles to the first and second guide bars 10 and 20 on the plane, the third guide bar 30 extending from the center point C by a predetermined length.

Here, the first, second and third guide bars 10, 20 and 30 has first, second and third guide grooves 11, 21 and 31 of predetermined widths and lengths formed from each end to the center point C in such a manner to correspond to the shape of the probe rods 40, 50 and 60. Particularly, the third guide bar 30 further has a fourth guide groove 31-1 of predetermined width and length formed between the third guide groove 31 and the center point C, and the fourth guide groove 31-1 is slidably connected to the moving part 70.

The third guide bar 30 guides motion of the third probe rod 60 at a position of the pelvis, in a state in which a patient lies on, to measure pubic of the pelvis. The first and second guide bars 10 and 20 guide motion of the first and second probe rods 40 and 50 at the position of the pelvis, in the state in which the patient lies on, to measure both lengths between two ASIS of the pelvis, preferably, in a horizontal direction uniformly with the floor and traversing the waist.

The first, second and third probe rods 40, 50 and 60 are respectively bent at the central portions at an angle of about 90 degrees. That is, the first, second and third probe rods 40, 50 and 60 are respectively divided at the bent portions into coupling parts 41, 51 and 61 corresponding to the guide grooves and slidably coupled with the guide grooves, and probe parts 42, 52 and 62 located in opposite directions of the coupling parts 41, 51 and 61 and located at a predetermined position of the pelvis. The coupling parts 41, 51 and 61 of the probe rods 40, 50 and 60 are controlled in the coupled lengths thereof in longitudinal directions of the corresponding guide grooves 11, 21 and 31 according to a size of the pelvis. Here, as the lengths of the probe parts 42, 52 and 62 (or height in a state in which the T-shaped supporter is connected) are the same, the plane formed by the guide bar 10, 20 and 30 of the T-shaped supporter 100 is even with an anterior pelvic plane formed at ends of the probe parts 42, 52 and 62. Namely, even though the probe rods 40, 50 and 60 moves along the guide grooves 11, 21 and 31, the anterior pelvic plane formed at the ends of the probe parts 42, 52 and 62 is always even with the plane formed by the guide bars 10, 20 and 30 of the T-shaped supporter.

Figure 2:
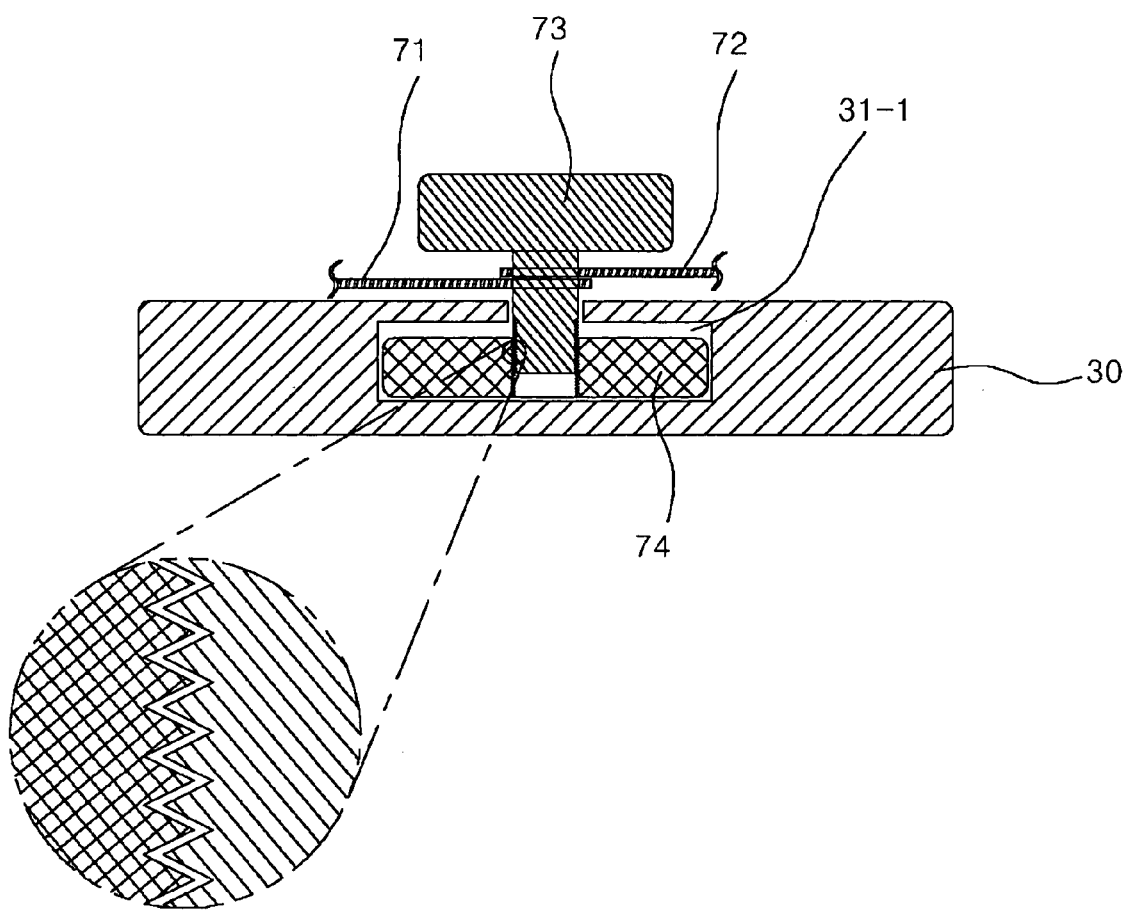
FIG. 2 is a sectional view taken by the line of A-A of FIG. 1.

As shown in FIG. 2, the moving part 70 includes a transfer fragment 74 mounted in the fourth guide groove 31-1, a first link 71 for connecting the first coupling part 41 coupled to the first guide groove 11 and the transfer fragment 74, and a second link 72 for connecting the second coupling part 51 coupled to the first guide groove 21 and the transfer fragment 74. Here, the first and second links 71 and 72 are rotatably connected to the transfer fragment 74 by a first rotation fixing member 73 like a bolt. That is, the first rotation fixing member 73 and the transfer fragment 74 are coupled by a bolt-and-nut coupling, and the first and second links 71 and 72 are rotatably connected to a body of the first rotation fixing member 73. Additionally, the other ends of the first and second links 71 and 72 are rotatably connected to the first and second coupling parts 41 and 51 by fixing elements 73-1 and 73-2.

Figure 4:
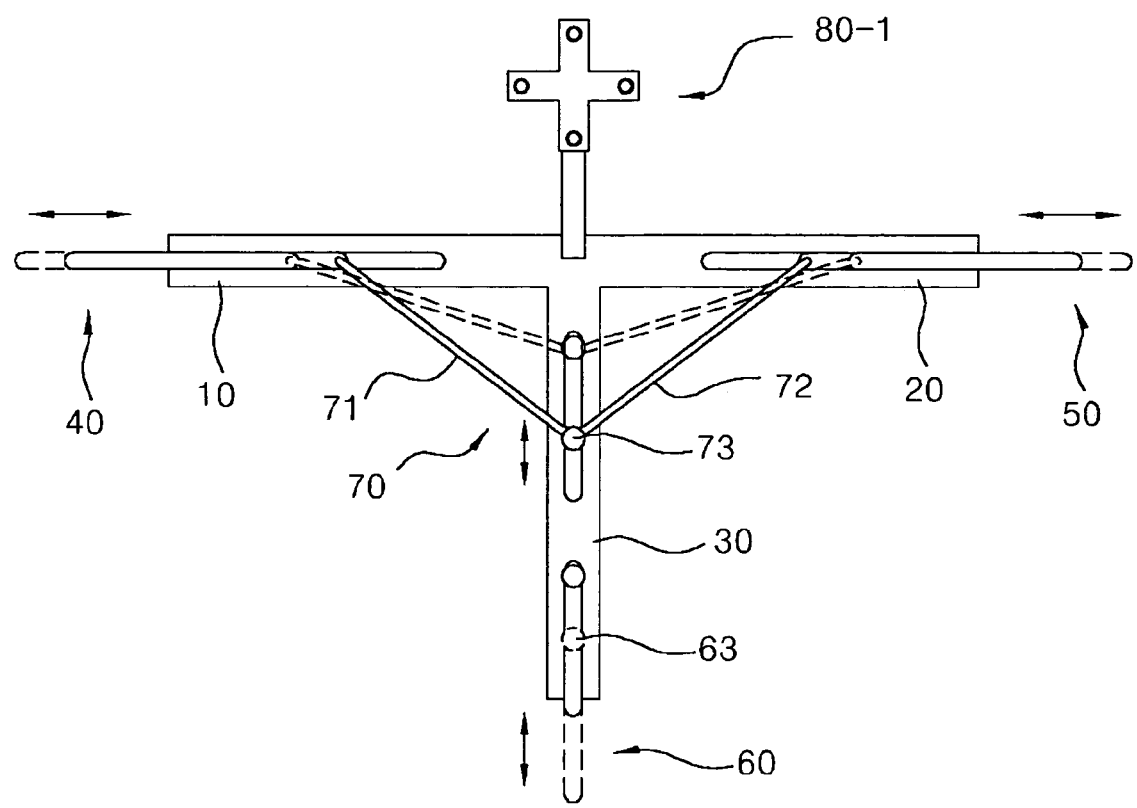
FIG. 4 is a structural view showing an operation state of the T-shaped gauge.

Therefore, as shown in FIG. 4, the coupling part 41 of the first probe rod 40 and the coupling part 51 of the second probe rod 50 are moved symmetrically from the transfer fragment 74 by the first and second links 71 and 72 and fixed at a predetermined position of the second guide groove 31-1 by the first rotation fixing member 73.

Figure 3:
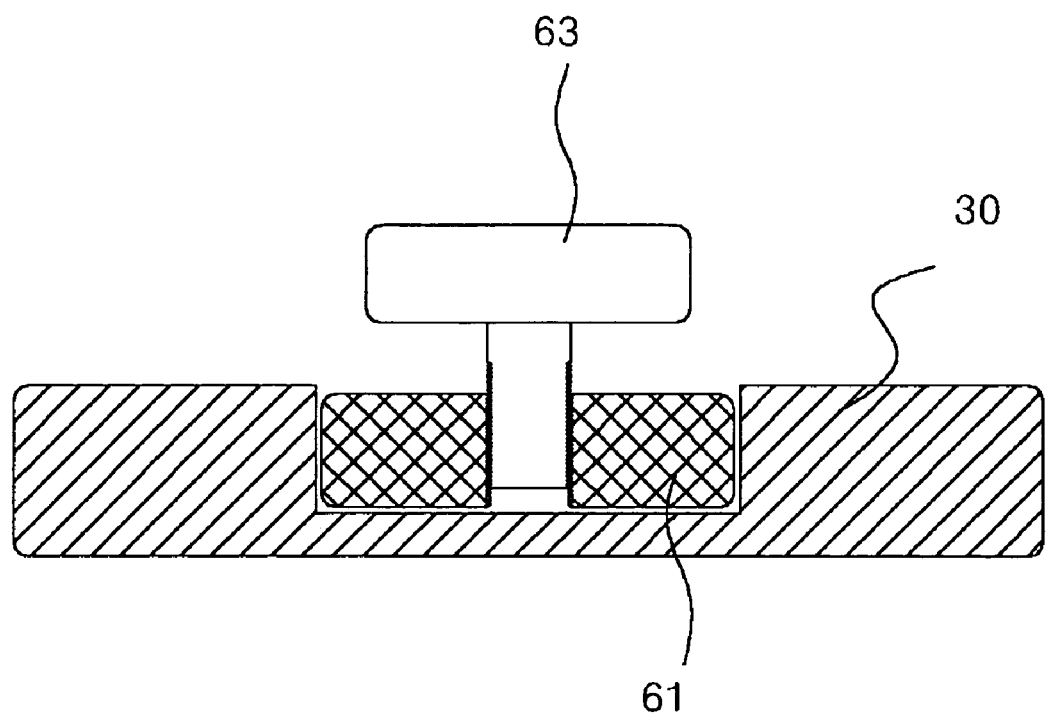
FIG. 3 is a sectional view taken by the line of B-B of FIG. 1.

Meanwhile, as shown in FIG. 3, the third coupling part 61 of the third probe rod 60 is fixed at a predetermined position of the third guide groove 31 by a second rotation fixing member 63 when the third probe part 62 is located at a predetermined point. Therefore, as shown in FIG. 4, the second probe rod 60 is moved in an axial direction of the third guide bar 30, and then, fixed at a position of the third guide bar 30.

Meanwhile, as shown in FIGS. 1A and 1B, the first dynamic reference base 80-1 includes a fixing member 82-1 having an end separably adhered onto a portion of the T-shaped supporter 100, a cross-shaped flat plate 83-1 connected to the other end of the fixing member 82-1, and light generators 81-1 adhered onto each end of the flat plate 83-1 for emitting light.

Here, as the light generators 81-1 are mounted at ends of the cross-shaped flat plate 83-1 one by one, the first dynamic reference base 80-1 has four light generators 81-1. Moreover, in this embodiment of the present invention, the light generators 81-1 are embodied by infrared emitting diodes (IREDs).

Figure 5:
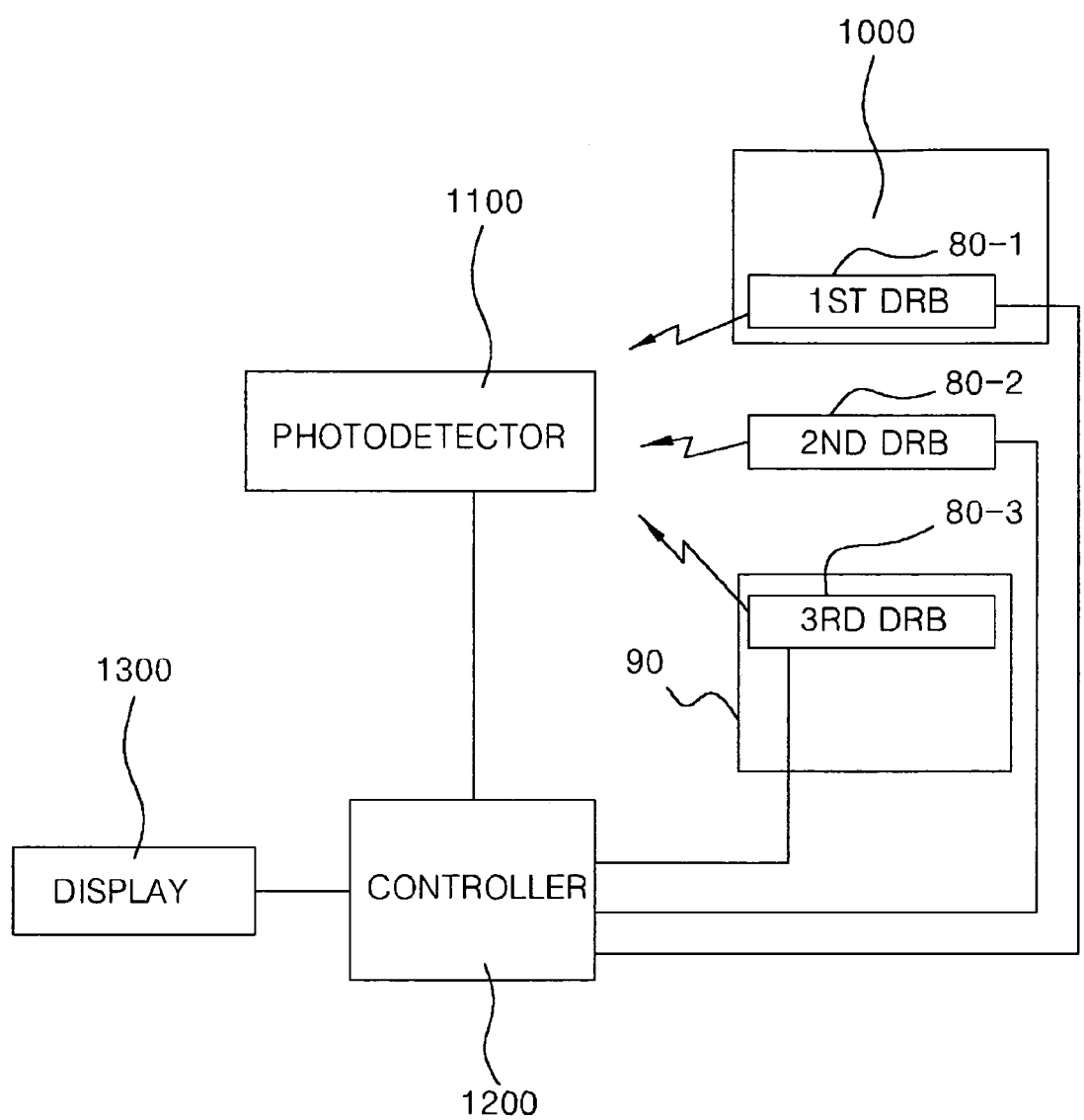
FIG. 5 is a structural view of an acetabular cup navigation system using the T-shaped gauge according to the present invention.

FIG. 5 is a structural view of an acetabular cup navigation system using the T-shaped gauge according to the present invention. The navigation system includes: a T-shaped gauge 1000 mounted at anatomical landmarks of the pelvis for indicating the anterior pelvic plane of the pelvis by emitting light; a second dynamic reference base 80-2 mounted on the pelvis for indicating a position of the pelvis; an acetabular cup positioner 90 for indicating a position of the acetabular cup, which will be inserted into the acetabulum of the pelvis; a photodetector 1100 for detecting light emitted from the first dynamic reference base 80-1 and the second dynamic reference base 80-2 of the T-shaped gauge 1000, and a third dynamic reference base 80-3 of the acetabular cup positioner 90; a controller 1200 for supplying power source to each part and obtaining three-dimensional information of the anterior pelvic plane, position information of the pelvis and position information of the acetabular cup; and a display 1300 for indicating information outputted from the controller 1200 into a type like GUI (Graphic User Interface).

Here, the T-shaped gauge 1000 has the same structure as FIGS. 1 to 4, and the anterior pelvic plane means a plane formed by the probe parts 42, 52 and 62.

Figure 6:
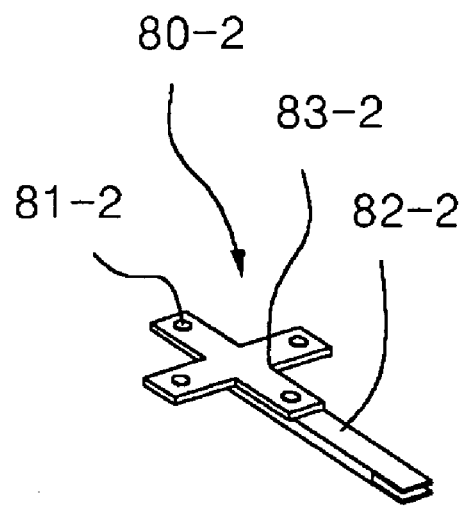
FIG. 6 is a structural view of the second dynamic reference base, which will be mounted on the pelvis.

As shown in FIG. 6, the second dynamic reference base includes a fixing member 82-2 having an end separably adhered onto a portion of the pelvis, a cross-shaped flat plate 83-2 connected to the other end of the fixing member 82-2, and light generators 81-2 adhered onto each end of the flat plate 83-2 for emitting light.

Figure 7:
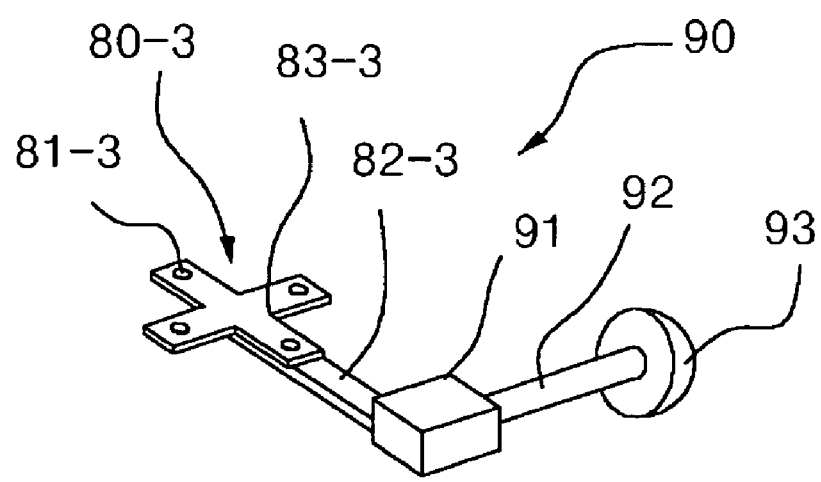
FIG. 7 is a structural view of an acetabular cup locator, which will be mounted on the pelvis.

As shown in FIG. 7, the acetabular cup positioner 90 includes the third dynamic reference base 80-3 for emitting light, an acetabular cup fixing part 93 for fixing the acetabular cup, and a fixing part 91 for integrally fixing the third dynamic reference base 80-3 with the acetabular cup fixing part 93. Here, the acetabular cup fixing part 93 is fixed to the fixing part 91 by a rod 92 of a predetermined length. Additionally, the third dynamic reference base 80-3, as in the first and second dynamic reference bases 80-1 and 80-2, includes a fixing member 82-3 having an end separably adhered onto a portion of the fixing part, a cross-shaped flat plate 83-3 connected to the other end of the fixing member 82-3, and light generators 81-3 adhered onto each end of the flat plate 83-3 for emitting light.

Meanwhile, the first to third dynamic reference bases 80-1, 80-2 and 80-3 have similar structures to each other, but the first dynamic reference base 80-1 is mounted on the T-shaped supporter 1000, the second dynamic reference base 80-2 is mounted on the pelvis, and the third dynamic reference base 80-3 is mounted on the acetabular cup positioner 90.

The acetabular cup navigation system and its operating method using the T-shaped gauge according to the present invention will be hereinafter described.

Figure 8:
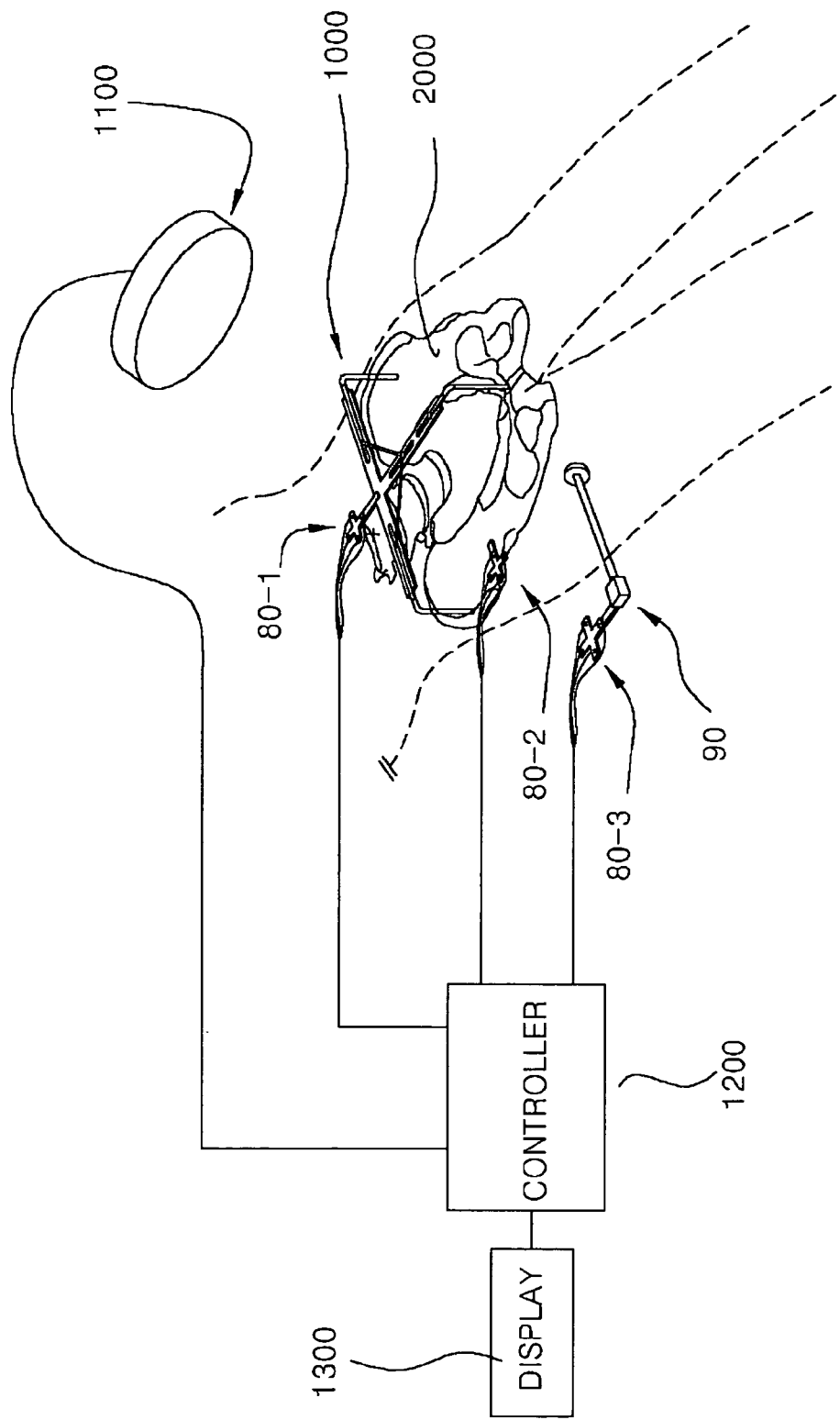
FIG. 8 is a structural view showing a state in which the acetabular cup navigation system using the T-shaped gauge according to the present invention is installed on the pelvis.

First, as shown in FIG. 8, inserted the second dynamic reference base 80-2 at the incised portion of pelvis, and then the probe parts 42, 52 and 62 of the T-shaped gauge 1000 are mounted at the peculiar points of the pelvis, and then the first dynamic reference base 80-1 is fixed to the T-shaped supporter to detect light emitted from the light generator 81-1 of the first dynamic reference base 80-1 by the photodetector 1100. Next, when the first dynamic reference base 80-1 emits light to the photodetector 1100, the photodetector 1100 transmits a detection signal to the controller 1200. Then, the controller 1200 calculates the anterior pelvic plane formed by the probe parts 42, 52 and 62 based on the detection signal transmitted from the photodetector 1100.

After the calculation of the anterior pelvic plane, the second dynamic reference base 80-2 is mounted at a position of the pelvis 2000 to detect light emitted from the light generator 81-2 of the second dynamic reference base 80-2 by the photodetector 1100. Next, when the light generator 81-2 of the second dynamic reference base 80-2 sends light to the photodetector 1100, the photodetector 1100 transmits a detection signal to the controller 1200. Then, the controller 1200 produces the pelvic reference frame formed by the second dynamic reference base 80-2 based on the detection signal transmitted from the photodetector 1100.

After that, the controller 1200 converts coordinates of the anterior pelvic plane obtained through the first dynamic reference base 80-1 in comparison with the pelvic reference frame obtained through the second dynamic reference base 80-2, and produces a transformed anterior pelvic plane.

Here, because the transformed anterior pelvic plane moves the second dynamic reference base 80-2 fixed to the pelvis when the pelvis 2000 is moved, its relative position is not changed, and hence, the transformed anterior pelvic plane becomes a standard coordinate frame, which will be set on the pelvis. That is, even though the pelvis is moved during surgery, the transformed anterior pelvic plane is always kept uniformly.

Meanwhile, the acetabular cup positioner 90 is mounted around the acetabulum, and the photodetector 1100 transmits a detection signal to the controller 1200 when the light generator 81-3 of the third dynamic reference base 80-3 emits light. Then, the controller 1200 calculates the direction vector of the acetabular cup positioner (or direction vector of the acetabular cup) based on the detection signal transmitted from the photodetector 1100. After that, the controller 1200 anatomically aligns the direction vector of the acetabular cup on the converted anterior pelvic plane. That is, the direction vector of the acetabular cup is indicated on the transformed anterior pelvic plane, which is always kept uniformly to the pelvis.

Therefore, in a state in which the direction vector of the acetabular cup is set on the transformed anterior pelvic plane, which always keeps its pelvis coordinates uniformly without regard to movement of the pelvis, the artificial joint surgery is performed. Namely, even though light emitted from the second dynamic reference base 80-2 to the photodetector 1100 is changed by moving the pelvis during the artificial joint surgery, the controller 1200 calculates the changed detection signal outputted from the photodetector in real time, and then, keeps the transformed anterior pelvic plane uniformly.

Meanwhile, as the acetabular cup positioner 90 has the relative position changed according to the movement of the pelvis, the direction vector of the acetabular cup is also changed. At this time, the controller 1200 calculates the changed direction vector of the acetabular cup in real time, indicates it on the transformed anterior pelvic plane, and outputs the calculated value to the display 1300 in the GUI form. Then, a doctor who is performing the surgery now, can check the direction of the acetabular cup inserted into the acetabulum visually through the display 1300.

Therefore, the acetabular cup navigation system using the T-shaped gauge according to the present invention forms the anterior pelvic plane using the value obtained by measuring the three anatomical landmarks of the pelvis via the T-shaped gauge at the same time, forms the converted anterior pelvic plane by transforming the anterior pelvic plane in comparison with the pelvic reference frame, and sets the direction vector of the acetabular cup on the transformed anterior pelvic plane, thereby exactly calculating the direction of the acetabular cup, which will be inserted into the acetabulum of the pelvis, without regard to the movement of the pelvis and displaying the calculated value on the display. So, the navigation system using the T-shaped gauge of the present invention can increase an accuracy of the artificial joint surgery.

Meanwhile, the acetabular cup navigation system using the T-shaped gauge according to the present invention can prevent a variation due to various pelvis sizes, prevent an increase in surgery costs, and reduce a danger of re-surgery, as not taking a CT scan process, which has been carried out by the conventional navigation systems, and not using the doctor's experiences and the mechanical guage provided by the artificial joint manufacturer.

In this embodiment of the present invention, the shape of the T-shaped supporter 100 of the T-shaped gauge 1000 is in the form of an alphabet letter 'T', but may be in the form of an alphabet letter 'Y' or an alphabet letter 'H' or '+' shape, which has four axial directions.

In the embodiment of the present invention, the coupling parts 41, 51 and 61 of the probe rods 40, 50 and 60 are slidably connected to the guide bars 10, 20 and 30, but it will be appreciated that the coupling parts 41, 51 and 61 may separably clamped to the guide bars 10, 20 and 30 in such a manner as to control lengths drawn form the guide bars 10, 20 and 30. Moreover, the probe rods may be a measuring device, such as an ultrasound sensor for measuring linear displacement.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A T-shaped gauge comprising:
   a) first, second and third probe rods fixable at three positions of a pelvis, the three positions forming a first plane;
   b) a T-shaped supporter slidably connected to the first, second and third probe rods to change the distance between ends of the probe rods, the T-shaped supporter being supported from the first plane to a predetermined height by the probe rods, wherein the T-shaped supporter comprises:
      i) first and second guide bars of predetermined widths, the first and second guide bars being formed coaxially on a second plane and extending in opposite directions from a center point, and
      ii) a third guide bar of a predetermined width located on the second plane and at right angles to the first and second guide bars on the second plane, the third guide bar extending from the center point by a predetermined length,
      wherein the first guide bar corresponds to the first probe rod along a first axis and comprises a first guide groove, the second guide bar corresponds to the second probe rod along a second axis and comprises a second guide groove, and the third guide bar corresponds to the third probe rod along a third axis and comprises a third guide groove, with the first, second, and third axes intersecting at the center point, and
      wherein the third guide bar further comprises a fourth guide groove of predetermined width and length formed between the third guide groove and the center point;
   c) a first dynamic reference base separably mounted at a portion of the T-shaped supporter, the first dynamic reference base emitting light to indicate the first plane; and
   d) a moving part moved symmetrically from the T-shaped supporter by the first and second probe rods, wherein the moving part comprises:
      i) a transfer fragment mounted in the fourth guide groove and reciprocating axially,
      ii) a first link moveably connected to both the transfer fragment and the first probe rod which is coupled to the first guide groove, and
      iii) a second link moveably connected to both the transfer fragment and the second probe rod which is coupled to the second guide groove.

2. The T-shaped gauge according to claim 1, wherein the first dynamic reference base includes:
   a fixing member having a first end separably mounted to the T-shaped supporter;
   a cross-shaped flat plate connected to a second end of the fixing member; and
   light generators mounted at ends of the flat plate respectively for emitting light.

* * * * *